(12) United States Patent
Hill

(10) Patent No.: US 6,453,194 B1
(45) Date of Patent: Sep. 17, 2002

(54) METHOD OF MEASURING CONSUMER REACTION WHILE PARTICIPATING IN A CONSUMER ACTIVITY

(76) Inventor: Daniel A. Hill, 1268 Pennsylvania Ave., Apt. 2, San Diego, CA (US) 92103

( * ) Notice: Subject to any disclaimer, the term of this patent is extended or adjusted under 35 U.S.C. 154(b) by 0 days.

(21) Appl. No.: 09/818,702

(22) Filed: Mar. 27, 2001

Related U.S. Application Data
(60) Provisional application No. 60/192,947, filed on Mar. 29, 2000.

(51) Int. Cl.[7] .............................. A61B 5/04; A61B 5/00
(52) U.S. Cl. ........................ 600/546; 600/301; 128/898
(58) Field of Search .............................. 600/26–28, 300, 600/301, 546, 547, 558, 559, 306, 307; 128/897, 898; 434/236

(56) References Cited

U.S. PATENT DOCUMENTS

| | | | | |
|---|---|---|---|---|
| 3,034,500 A | * | 5/1962 | Backster, Jr. ................ | 600/547 |
| 3,548,806 A | * | 12/1970 | Fisher .......................... | 600/484 |
| 3,870,034 A | | 3/1975 | James .......................... | 600/547 |
| 4,448,203 A | | 5/1984 | Williamson et al. ......... | 600/546 |
| 4,794,533 A | | 12/1988 | Cohen .......................... | 600/544 |
| 4,807,642 A | | 2/1989 | Brown ......................... | 600/546 |
| 4,817,628 A | | 4/1989 | Zealear et al. ............... | 600/554 |
| 4,964,411 A | | 10/1990 | Johnson et al. .............. | 600/546 |
| 5,092,343 A | | 3/1992 | Spitzer et al. ............... | 600/515 |
| 5,219,322 A | * | 6/1993 | Weathers ..................... | 600/27 |
| 5,247,938 A | | 9/1993 | Silverstein et al. .......... | 600/459 |
| 5,663,900 A | | 9/1997 | Bhandari et al. ............. | 1/1 |
| 5,676,138 A | | 10/1997 | Zawilinski ................... | 600/301 |
| 5,725,472 A | | 3/1998 | Weathers ...................... | 600/21 |
| 5,741,217 A | | 4/1998 | Gero ............................ | 600/547 |
| 5,772,591 A | | 6/1998 | Cram ........................... | 600/383 |
| 6,004,312 A | | 12/1999 | Finneran et al. ............. | 604/546 |
| 6,026,321 A | | 2/2000 | Miyata et al. ............... | 600/546 |
| 6,026,322 A | | 2/2000 | Korenman et al. .......... | 600/547 |
| 6,309,342 B1 | * | 10/2001 | Blazey et al. ................ | 600/26 |

* cited by examiner

*Primary Examiner*—Kevin Shaver
*Assistant Examiner*—Charles Marmor, II
(74) *Attorney, Agent, or Firm*—Michael S. Sherrill

(57) ABSTRACT

A sample population including a plurality of members participate in a consumer activity for a participation period to assess consumer reaction to the consumer activity. Surface electromyography signals from a zygomatic muscle and electrodermography signals of each member of the sample population are measured during the participation period. Data is recorded including at least a description of a stimulus experienced by each member during the participation period and a description of the interaction between the member and the stimulus. The recorded data is synchronized with the measurements of electromyography signals and electrodermography signals for each member to allow association of the recorded data with the measurements. The electromyography signals are equated or translated to an appeal value and the electrodermography signals are equated or translated to an impact value for each member. At least one of the appeal and impact values are visually represented, identified with the synchronously recorded stimulus.

19 Claims, No Drawings

METHOD OF MEASURING CONSUMER REACTION WHILE PARTICIPATING IN A CONSUMER ACTIVITY

This application claims the benefit of U.S. Provisional Application No. 60/192,947, filed Mar. 29, 2000.

FIELD OF THE INVENTION

The invention relates to methods of measuring consumer reaction to participation in a consumer activity.

BACKGROUND

Consumer reaction to a marketing stimulus (e.g., a television commercial) is typically assessed by means of exposing members of a focus group to the marketing stimulus (e.g., having the focus group watch the commercial) and obtaining the reactions and comments of the members immediately after exposure to the marketing stimulus by means of a written questionnaire and/or a personal interview. While generally effective, such a technique suffers from several drawbacks, including a tendency for members of a focus group to express inaccurately or imprecisely their reaction to the marketing stimulus.

The study of consumer reaction is generally restricted to exposing members of a focus group to predetermined marketing stimuli (i.e., forced selection) in order to ensure that the feed-back from the member corresponds to the defined marketing stimuli. It has long been recognized that the data obtained from such forced selection testing does not accurately reflect consumer experience as the member is not allowed to selectively interact with the marketing stimuli.

Hence, a longstanding need exists for a more reliable, scientific technique and methodology for measuring consumer reaction to participation in a consumer activity.

SUMMARY OF THE INVENTION

The invention is directed to a method of assessing consumer reaction to participation in a consumer activity, involving the steps of (a) allowing a sample population of at least two members to participate in a consumer activity for a period of time, (b) measuring surface electromyography signals from a zygomatic muscle of each member of the sample population during the participation period, (c) optionally measuring surface electromyography signals from a corrugator facial muscle of each member of the sample population during the participation period and combining the measured surface electromyography signals from the zygomatic and corrugator facial muscle of each member of the sample population to produce combined electromyography signals, (d) measuring electrodermography signals, selected from at least one of galvanic skin response signals, skin conductance level signals and skin resistance level signals, of each member of the sample population during the participation period, (e) recording data including at least a description of a stimulus experienced by each member during the participation period and a description of the interaction between the member and the stimulus, (f) synchronizing the recorded data with the measurements of electromyography signals and electrodermography signals for each member so as to allow association of the recorded data with measurements of electromyography signals and electrodermography signals, (g) equating or translating the electromyography signals to an appeal value for each member, (h) equating or translating the electrodermography signals to an impact value for each member, and (j) visually representing at least one of the appeal and impact values identified with the synchronously recorded stimulus.

By visually representing the appeal and impact values together for a given consumer activity for a given member (hereinafter "member set of appeal and impact values") on a single illustration, the overall relative marketing value of the stimuli involved in the consumer activity (i.e., extent to which consumers were impacted and whether such impact was favorable or unfavorable) can be understood. When desired, the group appeal and impact values can be determined with the group appeal and group impact values visually represented on a single illustration.

The method preferably involves repeating steps (a) through (h) for several different consumer activities with members of the sample group, and then visually comparing sets of appeal and the impact values for each of the consumer activities and/or specific stimuli with which the members interacted so as to allow a relative comparison of the consumer activities and/or the specific stimuli.

DETAILED DESCRIPTION OF THE INVENTION INCLUDING A BEST MODE

Definitions

As utilized herein, including the claims, the phrase "participation in a consumer activity" means substantially unrestrained action, involving an ability to decide when and how to proceed within a given consumer environment, optionally preceded by instruction or guidance as to type of action desired (e.g., navigating a retail store environment; interacting with an electronic kiosk such as an ATM, strolling through an amusement park, customer interaction with company employees; searching on the world wide web; opening, using or otherwise interacting with a product; etc.).

As utilized herein, including the claims, the phrase "group appeal value" means a middle appeal value representative of a plurality of appeal values, selected from the various options for selecting or calculating a middle value including specifically, but not exclusively mean, median, mode and norm.

As utilized herein, including the claims, the phrase "group impact value" means a middle impact value representative of a plurality of impact values, selected from the various options for selecting or calculating a middle value including specifically, but not exclusively mean, median, mode and norm.

As utilized herein, including the claims, the term "average" means a middle value representative of a plurality of values, selected from the various options for selecting or calculating a middle value including specifically, but not exclusively mean, median, mode and norm.

As utilized herein, including the claims, the phrase "zygomatic muscle" includes zygomaticus major and zygomaticus minor.

As utilized herein, including the claims, the phrase "set of appeal and impact values" means the combination of an appeal value and an impact value obtained for a single member (hereinafter referenced as "member set of appeal and impact values") or the combination of an average appeal value and an average impact value obtained for a group of members (hereinafter referenced as "group set of appeal and impact values").

As utilized herein, including the claims, the phrase "same type of consumer activity" means two or more consumer activities falling within one of (i) viewing and listening to television or motion picture, (ii) listening to music, (iii) listening to human speech, (iv) listening to sounds other than music or human speech, (v) viewing and listening to live performance, (vi) communicating face-to-face with a person, (vii) checking out at retail store, (viii) viewing print material, (ix) reading print material, (x) opening mail, (xi) viewing an internet site, (xii) moving around within a single internet site, (xiii) searching the internet, (xiv) viewing three-dimensional architecture and interior design, (xv) shopping in a retail store, (xvi) shopping in a shopping mall, (xvii) smelling fragrance, (xviii) viewing product, (xix) tasting product, (xx) touching product, (xxi) viewing construction of product, (xxii) receiving a service, (xxiii) opening product packaging, (xiv) using product, (xv) combinations of two or more of these activities, and (xvi) other.

As utilized herein, including the claims, the phrase "same type of goods or services" means goods or services which would be listed under the same topic heading in the most current US West Dex® Yellow Pages directory relative to the date of inquiry as to whether the goods or services are of the same type.

Method

A sample population must be chosen. The sample population may be chosen and prescreened according to any demographic, geographic or other marketing criteria of interest in accordance with the customary practice for selecting members of a focus group. The sample population must have at least two members, but may be as large as desired. Generally, a sample population of about 10 to 200 members, preferably 10 to 100 members, should provide statistically meaningful results at a reasonable cost. Sample populations having less than about 10 members tend to produce somewhat unreliable results, while sample populations of greater than about 200 significantly increase the cost of the study with only a modest improvement in reliability.

The members of the sample population are each attached ("wired") to an electrode for measuring electromyography activity (EMG) and an electrode for measuring electrodermal activity (EDA) by preparing the skin in accordance with standard preparatory protocols for removing oils and lowering electrode impedance, applying an electrode cream, and then attaching the electrodes to the skin of the member. EMG signals and their relation to muscle functions are relatively well understood. Briefly, muscles are controlled by nerves. Nerves cause contraction of muscles by transmitting an electrical signal to the muscle. A voltage change occurs when a muscle contracts, creating an electric potential that is directly proportional to the strength of the contraction. EMG electrodes measure this voltage change from the external surface area of the individual. The EMG electrode is positioned over a zygomatic (i.e., smile) muscle of the face. Optionally, additional EMG electrodes may also be positioned over one or more of (i) the zygomatic muscle on the other side of the face, (ii) a corrugator (i.e., frown) facial muscle on the same side of the face as the zygomatic muscle being monitored, and/or (iii) a corrugator facial muscle on the opposite side of the face from the zygomatic muscle being monitored.

EDA signals and their relation to sweat gland activity are similarly relatively well understood. Sweat gland activity increases as the strength of an individual's reaction to a stimulus increases. Sweat gland activity produces sweat, which results in a proportional increase in the galvanic, electrical conductance and electrical resistance of the skin. EDG electrodes measure this change in the skin. The EDG electrode may be positioned over any area of the body, with an industry preferences for the distal end of a finger.

The EMG and EDG electrodes are electrically connected to a suitable biofeedback system and central processing unit programmed to collect and report the EMG and EDG signals. Suitable biofeedback systems and central processing units for use in connection with EMG and EDG monitoring are available from a number of independent manufacturers. A suitable computerized biofeedback system is J&J Engineering model I-330 DSP. When participation in the consumer activity requires allowing the member of the sample population to move or wander within an environment (e.g., window shopping, grocery shopping or interacting with a product, etc.) the biofeedback system and central processing unit should be a portable unit which can be attached to the member. Suitable portable biofeedback systems include those available from Thought Technology Ltd. under the mark "MyoTrac2" and Atlas, Inc. under the mark "Minitor". Customized units can be purchased from UFI of Morro Bay, Calif., such as a 3992/3-EMG BioLog® System with a precision rectified EMG (2ch) and SCL.

The "wired" members are then allowed to participate in a consumer activity for a period of time, during which EMG signals from a first zygomatic muscle of the wired member and EDG signals from the wired member are collected. Such EMG and EDG signals may be collected for selected portions or throughout the entire participation period, with a preference for collecting such signals throughout the participation period.

Optionally EMG signals are collected from (i) a second zygomatic muscle on the other side of the face, (ii) a first corrugator facial muscle on the same side of the face as the first zygomatic muscle, and/or (iii) a second corrugator facial muscle on the opposite side of the face from the first zygomatic muscle. Any such additional EMG signals may be combined with the EMG signals from the first zygomatic muscle to produce a combined EMG signal. Since the EMG signals represent the appeal of the stimulus, with the zygomatic EMG signals representative of positive appeal and the corrugator EMG signals representative of negative appeal, the EMG signals should be combined by adding or averaging the zygomatic EMG signals when EMG signals from more than one zygomatic muscle are collected, adding or averaging the corrugator EMG signals when EMG signals from more than one corrugator muscle are collected, and then reducing the value of the zygomatic EMG signals by the value of the corrugator EMG signal value. The values of the zygomatic EMG signals, corrugator EMG signals and/or combined EMG signals may be conditioned by any desired constant for purposes of shifting the final values as considered appropriate for facilitating understanding of the visually represented appeal and/or impact values.

A preferred mathematical algorithm for combining EMG signals from zygomatic muscles and EMG signals from corrugator muscles is provided below as Equation 1 wherein the combined EMG-signal is a ratio of the difference between EMG signals from zygomatic muscle and EMG signals from corrugator muscle to the total EMG signals from zygomatic and corrugator muscles.

$$\text{Combined EMG} = \frac{(\text{EMG 1}^{st}\ \text{Zygo} + \text{EMG 2}^{nd}\ \text{Zygo}) - (\text{EMG 1}^{st}\ \text{Corr} + \text{EMG 2}^{nd}\ \text{Corr})}{(\text{EMG 1}^{st}\ \text{Zygo} + \text{EMG 2}^{nd}\ \text{Zygo}) + (\text{EMG 1}^{st}\ \text{Corr} + \text{EMG 2}^{nd}\ \text{Corr})} \quad \text{EQUATION 1}$$

The period of time during which members of the sample population are allowed to participate in a consumer activity can vary considerably depending upon a number of variables, including the type of goods and/or services involved, the type of media and the normal duration of exposure in the real world. Generally, an exposure period of between about 10 seconds to 10 minutes is sufficient. Of course, longer participation periods are possible in those instances where a longer participation period is necessary to accurately imitate actual consumer experience, such as when viewing the interior design of a shopping mall. Exposure periods of less than about 10 seconds do not always provide sufficient time for the members to fully participate in the consumer activity and physiologically react to the various stimuli encountered during the activity.

The EMG and EDG signals can be collected at any desired frequency from thousands of times a second to once every several seconds depending upon the desired information and time sensitivity of the stimulus (e.g, collection is required at a higher frequency when one of the goals of the testing is to determine how long to display each given scene in a television commercial).

The EMG and EDG signals can be collected throughout the participation period and a period of time before and after the participation period for purposes of establishing a base line and post stimulation level for the member. Establishing a base line and post simulation level for each member allows detailed analysis of the EMG and EDG signals, such as allowing the appeal and/or impact values to be visually represented in the form of a change in appeal and/or impact values resulting from participation in the consumer activity as well as the absolute value of the appeal and/or impact values.

The EMG signals, single or combined, are equated (ie., direct transfer) or translated (i.e., amplified, compressed, converted to a ratio, etc.) to an appeal value. Similarly, the EDG signals are equated or translated to an impact value.

Participation in a consumer activity provides members with options and choices as to the pace, method, manner and mode of observing and/or interacting with the various stimuli within the selected environment, including the possible choice of whether to observe and/or interact with a stimulus at all. In order to correlate the measured EMG and EDG signals with a particular stimulus or set of stimuli, the method includes the steps of (i) recording data, such as a description of the stimuli experienced by each member during the participation period and a description of the interaction between the member and the stimuli, and (ii) synchronizing such recorded data with the measurements of electromyography signals and electrodermography signals for each member.

A convenient method of recording such data is through the use of a video camera. A convenient option is for the video camera to be mounted on the head of the member and positioned to record what the member is viewing (e.g., worn as a cap or built into eyeglass frames). A suitable wireless observation system is available from Polaris Industries of Atlanta, Ga., such as an NAT-9 wireless camera and a GFR 5002 2.4 GHz wireless receiver. Another option is for an observer to shadow the member and record the member's activities with a video camera throughout the participation period. Any number of other alternatives are also available, such as use of a Dictaphone to record a verbal description of the member's actions. These options may also be used in combination as desired.

The recorded data can be synchronized with the measurements of electromyography signals and electrodermography signals by any of a number of techniques. One option is to simply start recording of data and measurement of electromyography signals and electrodermography signals at the same time, or at different times with a recording of the time difference between the two start times. One particularly effective technique is to simultaneously mark the recorded data and the measurements of electromyography signals and electrodermography signals at least once to establish an anchor point with respect to time. Such marking can be done electronically by generating a signal which is then simultaneously communicated to and recorded by both the biofeedback system and associated central processing unit and the data recording device (e.g., video cameras). Such marking can be done once or periodicallY throughout the participation period. It is also possible to allow an observer to randomly generate such anchor points at strategic times during the participation period (e.g., the start of the participation period, when the member first notices a defined stimulus, when the member first touches the stimulus and when the member first tastes the stimulus).

The recorded data can also include the length of time a member observed and/or interacted with a stimulus, as an additional measure of the member's interest in the stimulus.

The appeal value and impact value can then be visually represented, separately or in combination, preferably along with an identification of the synchronously recorded stimulus. The values may be representative of a single member of the sample population, the group value of a defined subset of the sample population (e.g., single males 20 to 30 years old, persons with an average household income of less than $40,000 per year, etc.), or the group value of the entire sample population. Standard rules of statistical analysis may be employed to the extent necessary and appropriate when group averages are represented.

The appeal and impact values may be visually represented in any desired manner, including specifically but not exclusively, in the form of a table, chart or graph (hereinafter collectively referenced as an "illustration"). The appeal and impact values may be represented on the same or separate illustrations.

The members of the sample population may be sequentially allowed to participate in different consumer activities, preferably the same type of consumer activity and for the same type of goods or services, for purposes of allowing a comparison of the set of appeal and the impact values for each of the consumer activities. When members are sequentially allowed to participate in different consumer activities, they should be given "down" time of at least several seconds between activities, during which time the member is not subjected to any stimuli or allowed to participate in any activity, for purposes of allowing the member to return to a base line.

I claim:

1. A method of assessing consumer reaction to a consumer activity, comprising:
   (a) allowing a sample population comprised of a plurality of members to participate in a consumer activity for a period of time;
   (b) measuring surface electromyography signals from a zygomatic muscle of each member of the sample population during the participation period;
   (c) measuring electrodermography signals, selected from at least one of galvanic skin response signals, skin conductance level signals and skin resistance level signals, of each member of the sample population during the participation period;
   (d) recording data including at least a description of a stimulus experienced by each member during the participation period and a description of the interaction between the member and the stimulus, and synchronizing such recorded data with the measurements of electromyography signals and electrodermography signals for each member so as to allow association of the recorded data with measurements of electromyography signals and electrodermography signals;

(e) equating or translating the electromyography signals to an appeal value for each member;

(f) equating or translating the electrodermography signals to an impact value for each member; and (g) visually representing at least one of the appeal and impact values identified with the synchronously recorded stimulus.

2. The method of claim 1 further comprising: measuring surface electromyography signals from a corrugator facial muscle of each member of the sample population during the participation period, and combining the measured surface electromyography signals from the zygomatic and corrugator facial muscle of each member of the sample population to produce a combined electromyography signal, wherein the combined electromyography signal is the electromyography signal equated or translated to the appeal value for each member.

3. The method of claim 2 wherein the combined surface electromyography signal is calculated by dividing the difference between the zygomatic and corrugator facial muscle signals by the sum of the zygomatic and corrugator facial muscle signals.

4. The method of claim 2 wherein electromyography signals are separately measured for bilateral zygomatic and corrugator facial muscles.

5. The method of claim 2 wherein electromyography signals are separately measured for zygomatic and corrugator facial muscles on the same side of the face.

6. The method of claim 1 further comprising visually representing at least one set of appeal and impact values of at least one member together on a single illustration.

7. The method of claim 6 further wherein at least one set of appeal and impact values of at least two members are visually represented together on a single illustration.

8. The method of claim 1 further comprising: repeating steps (a) through (f) with members of the sample population for at least one other consumer activity which is different from the first consumer activity, and visually comparing the set of appeal and impact values of each consumer activity.

9. The method of claim 8 wherein the consumer activities are of the same type.

10. The method of claim 8 wherein the consumer activity involves sales or marketing of the same type of goods or services.

11. The method of claim 8 wherein the sample population is comprised of between about 10 to 100 members.

12. The method of claim 8 wherein (i) a period of time is provided between participation in sequential consumer activities during which the members are not exposed to any stimuli nor provided with an opportunity to participate in a consumer activity, and (ii) the surface electromyography signals and electrodermal signals are measured throughout each participation period and for a period of time before and after each participation period.

13. The method of claim 1 wherein the sample population is comprised of between about 10 to 200 members.

14. The method of claim 1 wherein the surface electromyography signals and electrodermal signals are measured throughout the participation period, a period of time before the participation period and a period of time after the participation period.

15. The method of claim 1 wherein a group set of appeal and impact values is visually represented.

16. The method of claim 15 wherein the visually represented group set of appeal and impact values is an average appeal value and an average impact value for the sample population.

17. The method of claim 1 wherein electromyography signals are separately measured for bilateral zygomatic muscles of each member of the sample population during the participation period and the measured surface electromyography signals for the bilateral zygomatic muscles of each member of the sample population is combined to produce a combined electromyography signal, wherein the combined electromyography signal is the electromyography signal equated or translated to the appeal value for each member.

18. The method of claim 1 wherein data is recorded with a video camera.

19. The method of claim 1 wherein (i) data, electromyography signals and electrodermography signals are recorded, and measured as a function of time, and (ii) the recording of data is synchronized with the measurements of electromyography signals and electrodermography signals by simultaneously marking the recorded data and the measurements of electromyography signals and electrodermography signals at least once to establish an anchor point with respect to time.

* * * * *